United States Patent [19]
Williams

[11] Patent Number: 5,240,009
[45] Date of Patent: Aug. 31, 1993

[54] MEDICAL DEVICE WITH MORPHOLOGY DISCRIMINATION

[75] Inventor: Michael O. Williams, Sunnyvale, Calif.

[73] Assignee: Ventritex, Inc., Sunnyvale, Calif.

[21] Appl. No.: 674,116

[22] Filed: Mar. 25, 1991

[51] Int. Cl.⁵ .................................. A61B 5/0402
[52] U.S. Cl. ............................. 128/702; 364/413.06
[58] Field of Search .............. 128/696, 702, 704, 705, 128/703, 706, 708, 710; 364/413.06

[56] References Cited

U.S. PATENT DOCUMENTS

| | | | |
|---|---|---|---|
| T925,003 | 8/1974 | Bonner | 128/702 |
| 3,267,934 | 8/1966 | Thornton | 128/702 |
| 3,524,442 | 8/1970 | Horth | 128/703 |
| 3,757,398 | 12/1974 | Rubin et al. | 128/419 D |
| 3,829,766 | 8/1974 | Herz . | |
| 3,940,692 | 2/1976 | Neilson | 128/702 |
| 3,978,856 | 9/1976 | Michel | 128/705 |
| 4,073,011 | 2/1978 | Cherry et al. | 128/704 |
| 4,170,992 | 10/1979 | Dillman | 128/702 |
| 4,193,393 | 3/1980 | Schlager | 128/702 |
| 4,492,235 | 1/1985 | Sitrick | 128/706 |
| 4,552,154 | 11/1985 | Hartlaub | 128/702 |
| 4,680,708 | 7/1987 | Ambos | 128/703 |
| 4,721,114 | 1/1988 | DuFault et al. | 128/696 |
| 4,754,762 | 7/1988 | Stuchl | 128/702 |
| 4,825,869 | 5/1989 | Sasmor et al. | 128/419 PT |
| 4,893,632 | 1/1990 | Armington | 128/708 |
| 4,905,708 | 3/1990 | Davies | 128/419 PG |
| 4,977,899 | 12/1990 | Digby et al. | 128/702 |
| 5,014,701 | 5/1991 | Pless et al. | 128/419 PG |

OTHER PUBLICATIONS

"Detection of Pathological Tachycardia by Analysis of Electrogram Morphology", Davies D W., Wainwright R J, et al., PACE vol. 9 Mar.-Apr. 1986.
"Dual Lead Fibrillation Detection for Implantable Defibrillators via LMS Algorithm", DuFault R A, Wilcox A C, Proceedings of the Eighth Annual Conference of the IEEE/Engineering in Medicine and Biology Society.
"Tachycardia Detection in Implantable Antitachycardia Devices", Jenkins J., Bump T., et al., PACE vol. 7 Nov.-Dec. 1984 Part II.
"Temporal Electrogram Analysis: Algorithm Development", Paul V E, O'Nunain S., et al., PACE vol. 13 Dec. 1990, Part II.
"Identification of Ventricular Tachycardia With Use of The Morphology of the Endocardial Electrogram", Langberg J, Gibb W., et al., Therapy and Prevention-Arrhythmia vol. 77, No. 6 Jun. 1988.
"Identification of Ventricular Tachycardia Using Intracavitary Ventricular Electrograms: Analysis of Time and Frequency Domain Patterns", Lin D., Dicarlo L A, Jenkins J M, Pace vol. 11, Nov. 1988.
"Time Domain and Spectral Analysis of Electrograms in Man During Regular Ventricular Activity and Ventricular Fibrillation", Morkrid L, Ohm O, Engedal H, IEEE Transactions on Biomedical Engineering vol. BME-31 No. 4, Apr. 1984.

Primary Examiner—William E. Kamm
Assistant Examiner—Kennedy J. Schaetzle
Attorney, Agent, or Firm—Steven M. Mitchell; Mark J. Meltzer

[57] ABSTRACT

A medical device is provided for monitoring waveform complexes of intracardiac electrograms. The intracardiac electrogram is identified by determining, with respect to a waveform peak of the intracardiac electrogram, its amplitude, width and polarity. The identification criteria are averaged and stored to provide a standard complex. Subsequent complexes are compared to the stored standard complex. Such comparison includes comparing peaks of subsequent complexes with the peaks of a stored standard complex, aligning subsequent complexes with a stored standard complex, and providing a score associated with the comparisons and alignment.

23 Claims, 11 Drawing Sheets

Figure 1 Intracardiac Complex

MEDICAL DEVICE WITH MORPHOLOGY DISCRIMINATION

FIELD OF THE INVENTION

The present invention concerns a novel medical device and method for monitoring waveform complexes of intracardiac electrograms.[1]

[1]. An intracardiac electrogram (ICEG) is the electrical activity of the heart as seen by a cardiac sensing lead on or in the heart.

BACKGROUND OF THE INVENTION

It is very desirable to discriminate between normal cardiac rhythms and arrhythmias using a single, internally placed cardiac sensing lead. Previously, heart rate has typically been the criterion used for rhythm classification.

Using heart rate as the sole criterion for rhythm classification is problematic. Many physically active patients have heart rates during exercise that overlap with their tachycardia rates. Other patients exhibit supraventricular tachycardias, the rates of which overlap with rates of tachycardias of ventricular origin. These supraventricular tachycardias are often well tolerated and require no intervention.

When physicians classify an intracardiac rhythm, they examine the morphology of the electrocardiogram in addition to the heart rate. The shape of an intracardiac complex holds information on the origin and sequence of the heart's electrical activity. A normal intracardiac complex traverses the AV node and is conducted by specialized cardiac tissue throughout the ventricles This results in a distinctive complex morphology. A tachycardia of ventricular origin often has a very different morphology due to its ectopic origin and conductance through cardiac muscle tissue.

Sensing of the atria, in addition to the ventricles, would provide the most direct information on whether a complex was of normal or ventricular origin.[2] This requires another sensing lead and more complex sensing electronics. Currently available bradycardia pacemakers sense in both chambers but do so with the added cost of an additional sensing lead and device complexity.

[2]. "Tachycardia Detection in Implantable Antitachycardia Devices", Jenkins J., Bump T., et al., PACE Vol. 7 November-December 1984 Part II.

The use of multiple leads in the ventricles has been proposed This would allow a determination of the ventricular activation pattern and provide more information on the source and sequence of ventricular electrical activity.[3]

[3]. "Dual Lead Fibrillation Detection for Implantable Defibrillators via LMS Algorithm", DuFault RA, Wilcox AC, Proceedings of the Eighth Annual Conference of the IEEE/Engineering in Medicine and Biology Society.

The use of correlation programs to determine whether a complex matches a stored template has been proposed. This stored template is normally taken to be the normal intracardiac complex and a poor correlation to its shape is an indication of a tachyarrhythmia. These correlation programs require large amounts of computation and are unrealistic for the microprocessors and batteries used in today's implanted devices.[4]

[4]. "Time Domain and Spectral Analysis of Electrograms in Man During Regular Ventricular Activity and Ventricular Fibrillation", Morkrid L, Ohm O, Engedal H, IEEE Transactions on Biomedical Engineering Vol. BME-31 No. 4, April 1984.
"Identification of Ventricular Tachycardia Using Intracavitary Ventricular Electrograms: Analysis of Time and Frequency Domain Patterns", Lin D, Dicarlo LA, Jenkins JM, PACE Vol. 11, November 1988.

Many template generating and comparison schemes have been proposed and patented.[5] Many of these are concerned with templates consisting of discrete samples of the signal's amplitude.

[5]. Method and Apparatus for Comparing Waveform Shapes of Time-Varying Signals, U.S. Pat. No. 4,893,632.
Electrical Cardiac Defibrillator, U.S. Pat. No. 3,857,398.
System and Method for Predicting Ventricular Tachycardia by Derivative Analysis, U.S. Pat. No. 4,492,235.
Method and Apparatus for Analyzing Electrocardiographic Signals, U.S. Pat. No. 4,680,708.
Electrocardiogram Monitoring Apparatus, U.S. Pat. No. 3,829,766.

It has also been suggested that examination of the slopes of the peaks within the intracardiac complex can be used to discriminate between normal and tachyarrhythmic complexes.[6]

[6]. "Detection of Pathological Tachycardia by Analysis of Electrogram Morphology", Davies DW., Wainwright RJ, et al., PACE Vol. 9 March-April 1986.

An existing defibrillator uses a probability density function (PDF) as an additional criterion for rhythm classification. This is a measure of the time the heart spends at electrical rest. PDF is not based on the morphology of complexes.

It is an object of the present invention to provide an improved medical device such as a cardiac pacer or a cardiac defibrillator, with morphology discrimination.

Another object of the present invention is to provide a device and method for discriminating between intracardiac electrical activity of supraventricular origin and intracardiac electrical activity of ventricular origin.

A further object of the present invention is to provide a self-contained implantable medical device for monitoring waveform complexes of intracardiac electrograms, in a highly effective and efficient manner.

Other objects and advantages of the present invention will become apparent as the description proceeds.

SUMMARY OF THE INVENTION

In accordance with the present invention, a medical device is provided for monitoring waveform complexes of intracardiac electrograms. The device comprises electrode means adapted to be coupled to a patient's heart and sensing means having an input coupled to the electrode means for sensing analog intracardiac electrograms. Analog to digital converter means is provided for converting the analog intracardiac electrogram to digital form. Means are provided for examining the intracardiac electrogram. The examining means comprise means for determining, with respect to a waveform peak of the digitized intracardiac electrogram, its amplitude, width and polarity, to provide identification criteria. Means are provided for storing the identification criteria.

In the illustrative embodiment, means are provided for concluding if the examined peak is within the same waveform complex as the previous peak. The concluding means comprise means for determining whether the examined peak occurred within a predetermined time after the occurrence of a previously-identified peak, determining whether the examined peak occurred within a predetermined time after occurrence of a first identified peak of a new waveform complex, and determining whether a predetermined maximum number of peaks have occurred.

In an illustrative embodiment, the storing means is operable to store a standard waveform complex. To this end, a plurality of waveform complexes is averaged to provide the standard complex. The averaging means is operable periodically, when a predetermined number of waveform complexes have occurred. Means are provided for recognizing a significant change in the stored standard complex and for generating a new standard complex when a significant change has occurred.

In the illustrative embodiment, peaks of subsequent complexes are compared with peaks of a standard complex. Means are provided for aligning subsequent complexes with a stored standard complex and there are means for providing a score associated with the comparisons and alignment. The aligning means comprises means for determining maximum peaks for each complex, means for matching the polarities of the maximum peaks, and means for aligning (a) the dominant part of the complex having fewer peaks with (b) the dominant part of the complex having more peaks. The dominant part of a complex is understood to mean those central peaks of a complex which have amplitudes which exceed some predetermined threshold. The dominant part of a complex is the critical portion for alignment of complexes. It has been found that the preferred method of aligning two complexes having a different number of peaks in the dominant part is to set the complex with more peaks and adjust or align the complex with fewer peaks to it.

In the illustrative embodiment, the scoring that is provided has values that ar indicative of the similarity or dissimilarity of the compared peaks. Further, the scoring has values that are indicative of the nature of the compared peaks.

A more detailed explanation of the invention is provided in the following description and claims, and is illustrated in the accompanying drawings.

DESCRIPTION OF THE PREFERRED EMBODIMENT

Figure 1:
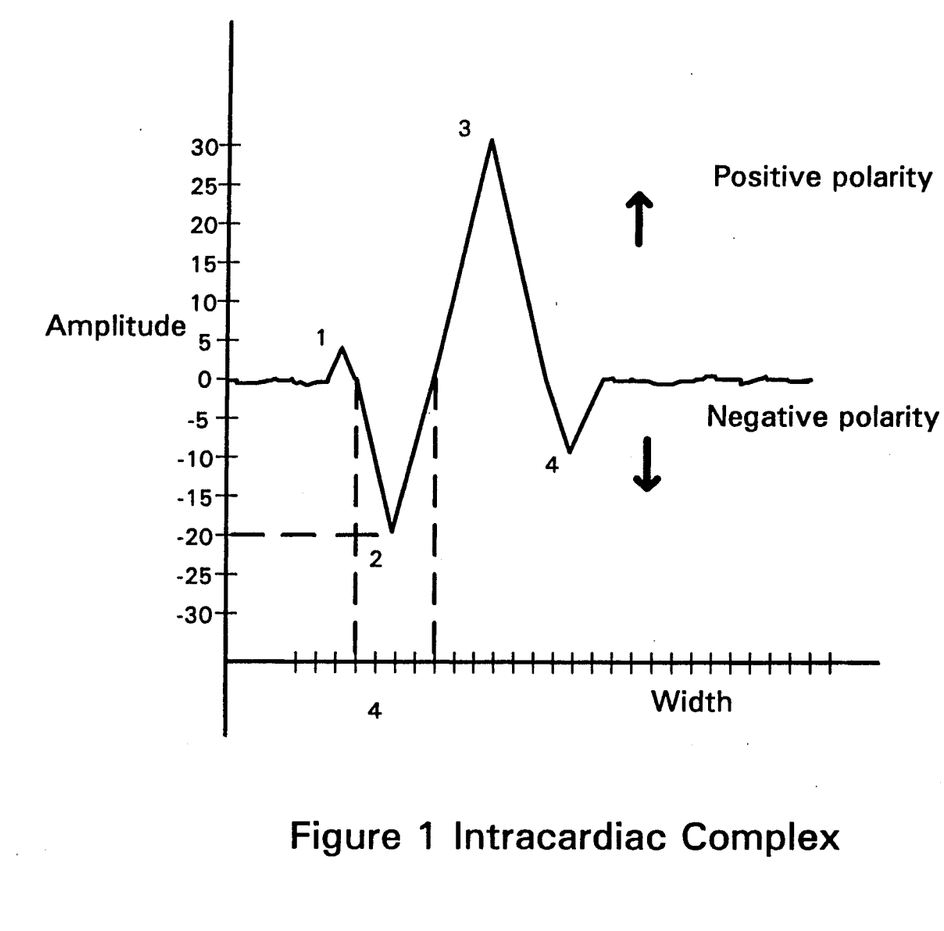
FIG. 1 is a diagram of a typical QRS complex from an intracardiac electrogram.

The present invention is able to extract features from the intracardiac electrogram. Referring to FIG. 1, each intracardiac complex comprises a number of peaks 1, 2, 3, 4. Each of these peaks has attributes associated with it that define its shape. Each peak has an amplitude, a polarity, and a width. For example, peak 2 has an amplitude of 20, a negative polarity and a width of 4. Each waveform complex can be defined as a series of peaks having an amplitude, a polarity and a width.

Figure 2:
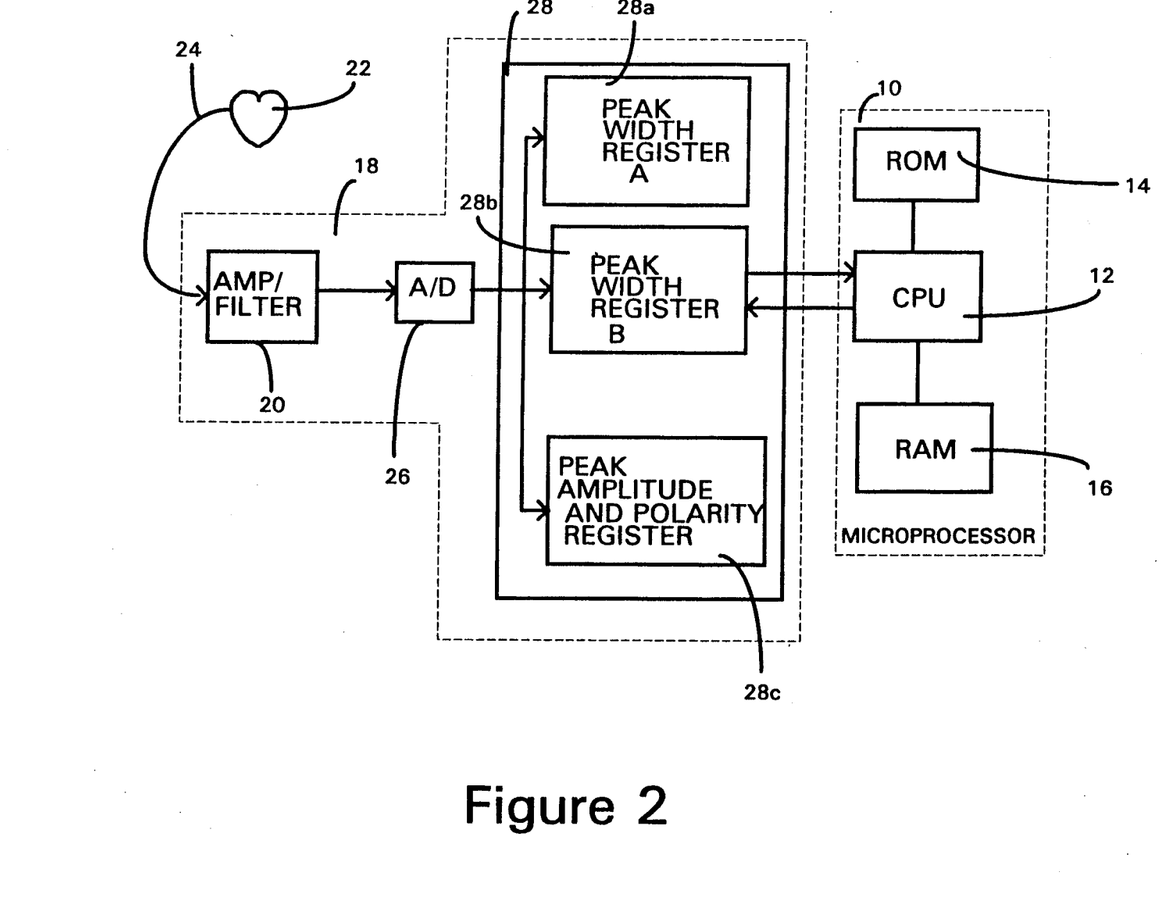
FIG. 2 is a block diagram of an implantable medical device constructed in accordance with the principles of the present invention.

A block diagram of a self-contained implantable defibrillator according to the system of the invention is illustrated in FIG. 2. Referring to FIG. 2, the microprocessor 10 has a conventional architecture comprising a CPU 12, A ROM 14, and RAM 16. The ROM 14 contains the program code that determines the operation of the device. The RAM 16 is used to store values which modify the operating characteristics of the device and working values needed to carry out the programs. Standard and subject complexes are also stored in the RAM 16 by the CPU 12. The CPU 12 performs the logical operations directed by the program code in the ROM 14.

Integrated circuit 18 is a microprocessor peripheral and provides sensing, digitization, waveform analysis, and timing functions. Electrogram sensing circuitry 20, including an amplifier and filter, interfaces with the ventricle of the heart 22 through line 24. This section amplifies and filters the sensed electrogram. The analog to digital converter 26 converts the analog waveforms from sensing circuitry 20 to digital values representing the amplitude of the analog signals. The waveform analysis circuits 28 extract peak amplitude, peak polarity and peak width information from the digitized data stream. The microprocessor 10 uses this information to discriminate arrhythmias from normal sinus rhythm. The waveform analyzer 28 incorporates an amplifier which can be controlled by the microprocessor 10. Different gain settings are used to keep the intracardiac electrogram within a useful amplitude range, in accordance with the invention disclosed in Carroll and Pless U.S. Pat. No. 4,972,835, issued Nov. 27, 1990.

Microprocessor 10 is able to set two threshold values (an upper and a lower threshold) within the waveform analyzer 28. These threshold values are amplitudes against which the digitized intracardiac electrocardiogram is compared.

Microprocessor 10 can read registers 28a, 28b and 28c within the waveform analyzer 2 which contain information about the most recently encountered peak. These registers 28a, 28b and 28c provide the data needed to characterize each peak. There are two width registers 28a and 28b available for CPU 12 to read. One width register 28a contains the number of milliseconds that the peak spent above the upper threshold, the other width register 28b contains the number of milliseconds spent above the lower threshold. There is a peak amplitude register 28c available for reading. The peak amplitude register 28c contains the peak amplitude seen for that peak so far. The peak amplitude register 28c also contains a sign bit which indicates the polarity of the peak.

Microprocessor 10 also selects the events which cause the microprocessor to begin execution of the ROM program. These events include the crossing of the two thresholds in the upward and downward directions (e.g. leading edge (upward) crossing of the lower threshold, trailing edge (downward) crossing of the upper threshold) and timeout of CPU initiated timers.

A detailed description of a representative waveform analyzer 28 can be found in Pless and Carroll U.S. patent application Ser. No. 354,138, filed May 19, 1989, now U.S. Pat. No. 5,014,701. The disclosure of application Ser. No. 354,138 is incorporated herein by reference.

An intracardiac complex is said to occur when the upper threshold in the waveform analyzer 28 is exceeded. Lower threshold peaks which are a part of that complex can occur before and after the upper threshold crossing. All of these lower threshold peaks must be captured as well. This is accomplished by executing a ROM program at every trailing edge crossing of the lower threshold. The data characterizing that peak (amplitude, polarity, and width) can then be read and stored.

Ensuing peaks must occur within a prescribed time window to be considered members of the same complex. This time window is externally variable and has a nominal value of 80 milliseconds. If a peak is captured outside this window it is deemed to be part of a different complex. For each complex there is a time limit and a limit on the number of peaks allowed. The time limit is externally variable and will nominally consist of a window extending 100 to 200 milliseconds from the first detected peak. Capturing of peaks is also terminated when data for some number (5 is used through this application as an example) of peaks has been stored (whether or not the allowed complex time limit has been reached).

Figure 3A:
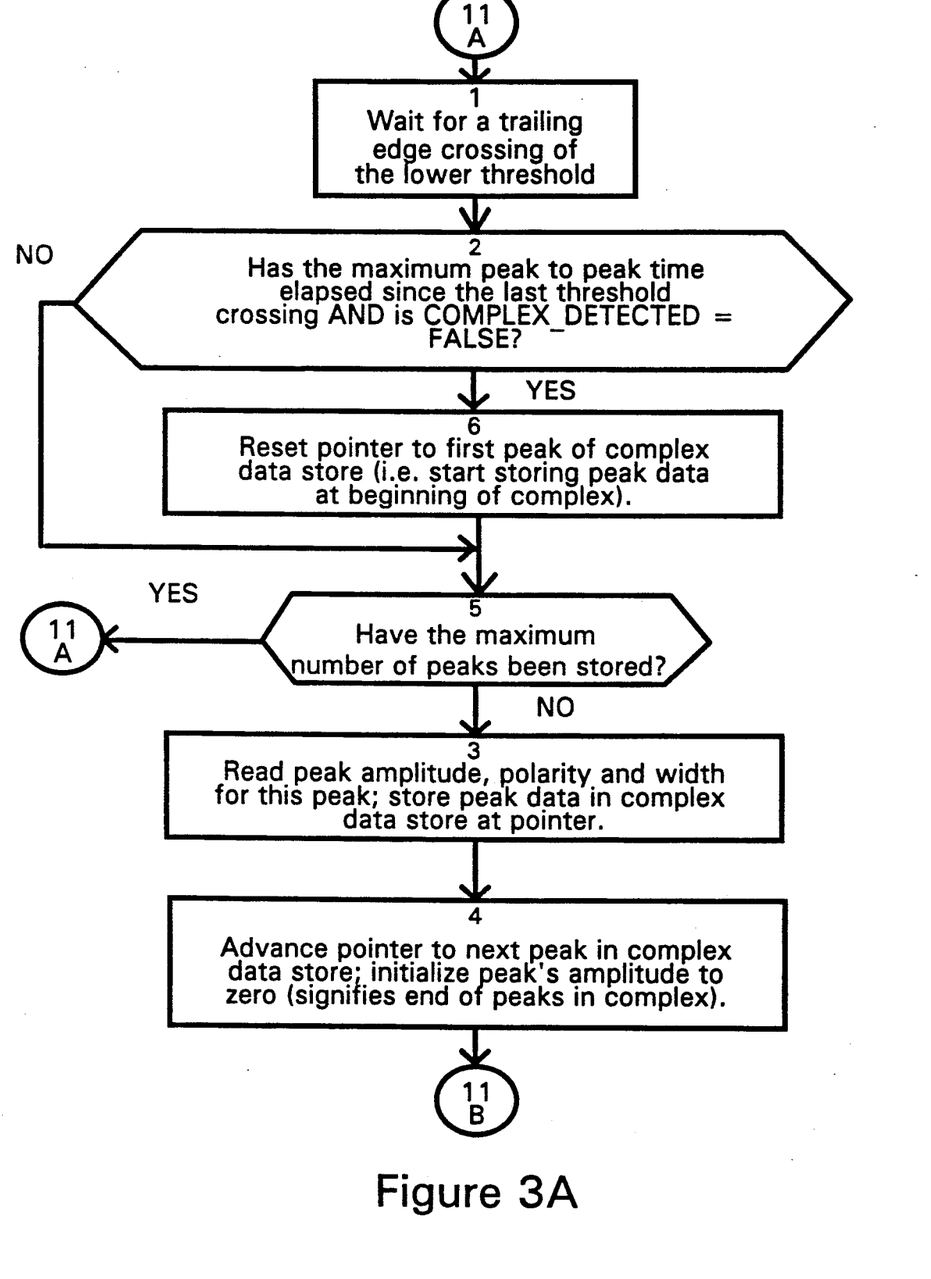
FIGS. 3A and 3B, When connected together, are a flow chart describing the capture of waveform complexes.
Figure 3B:
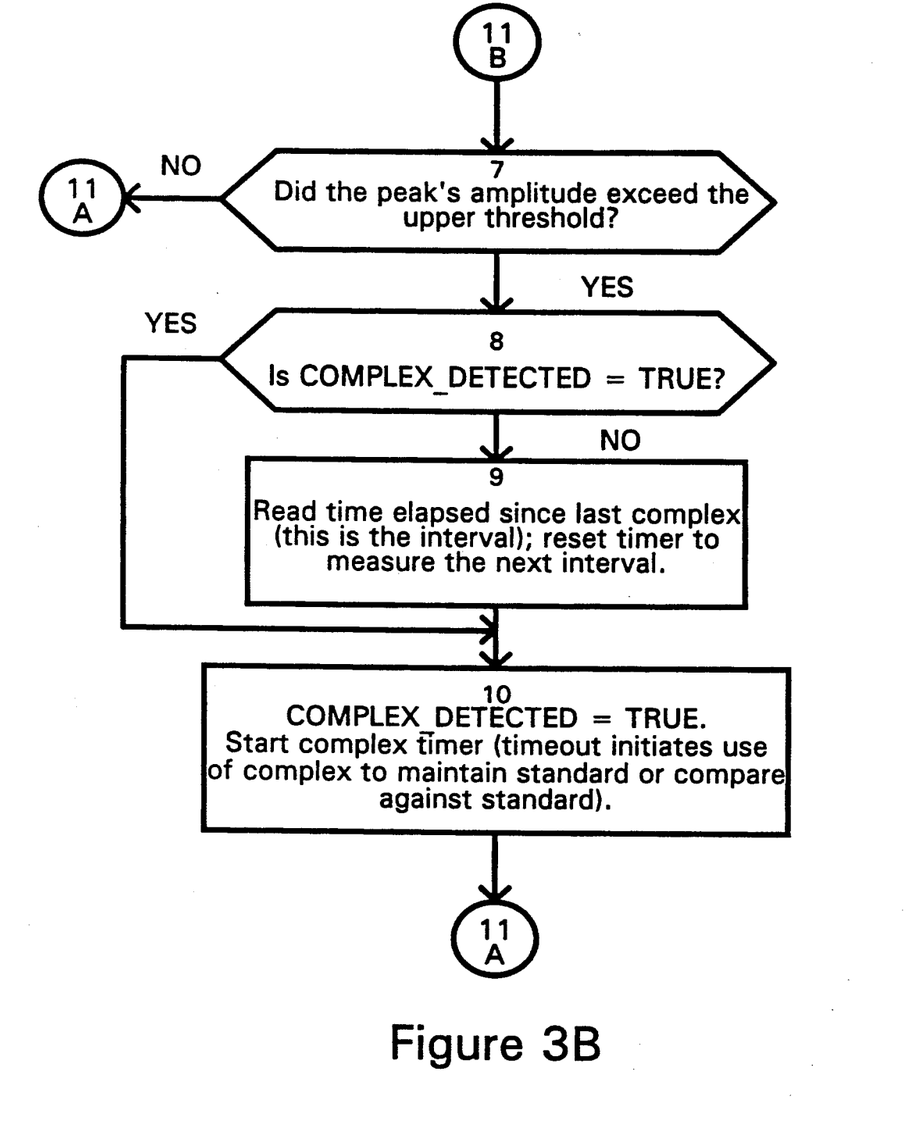
Figure 4A:
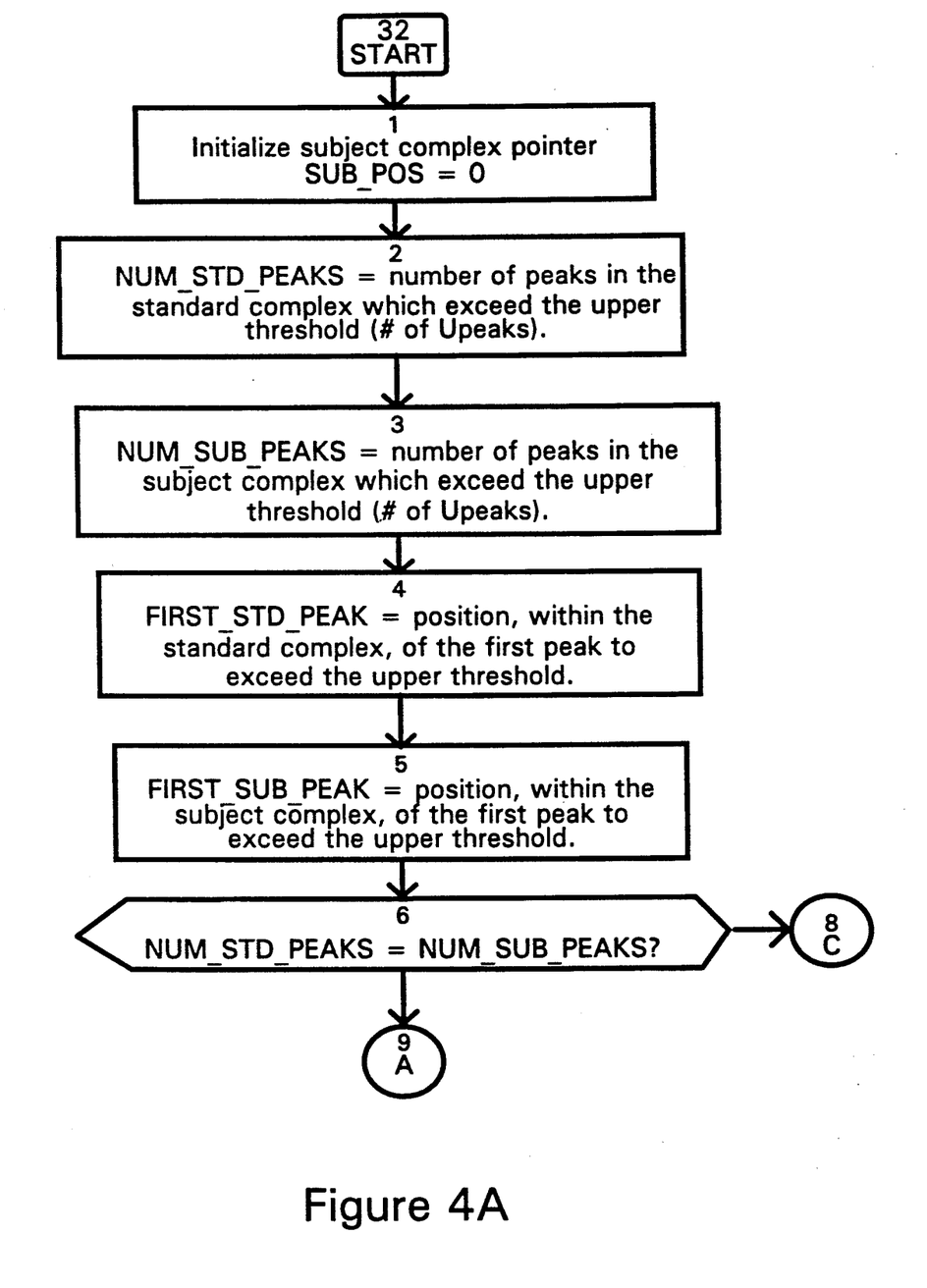
FIGS. 4A–4D, when connected together, are a flow chart describing the alignment of waveform complexes.
Figure 4B:
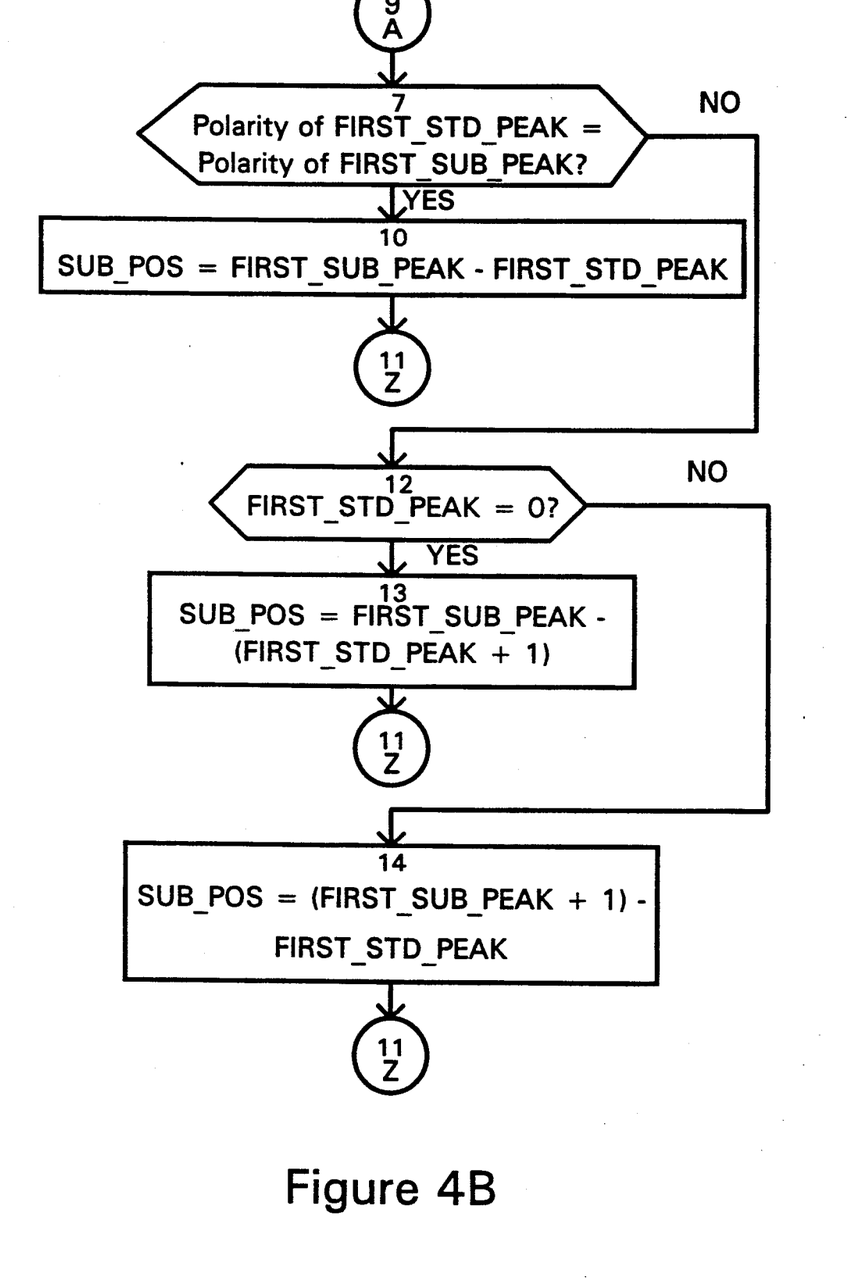
Figure 4C:
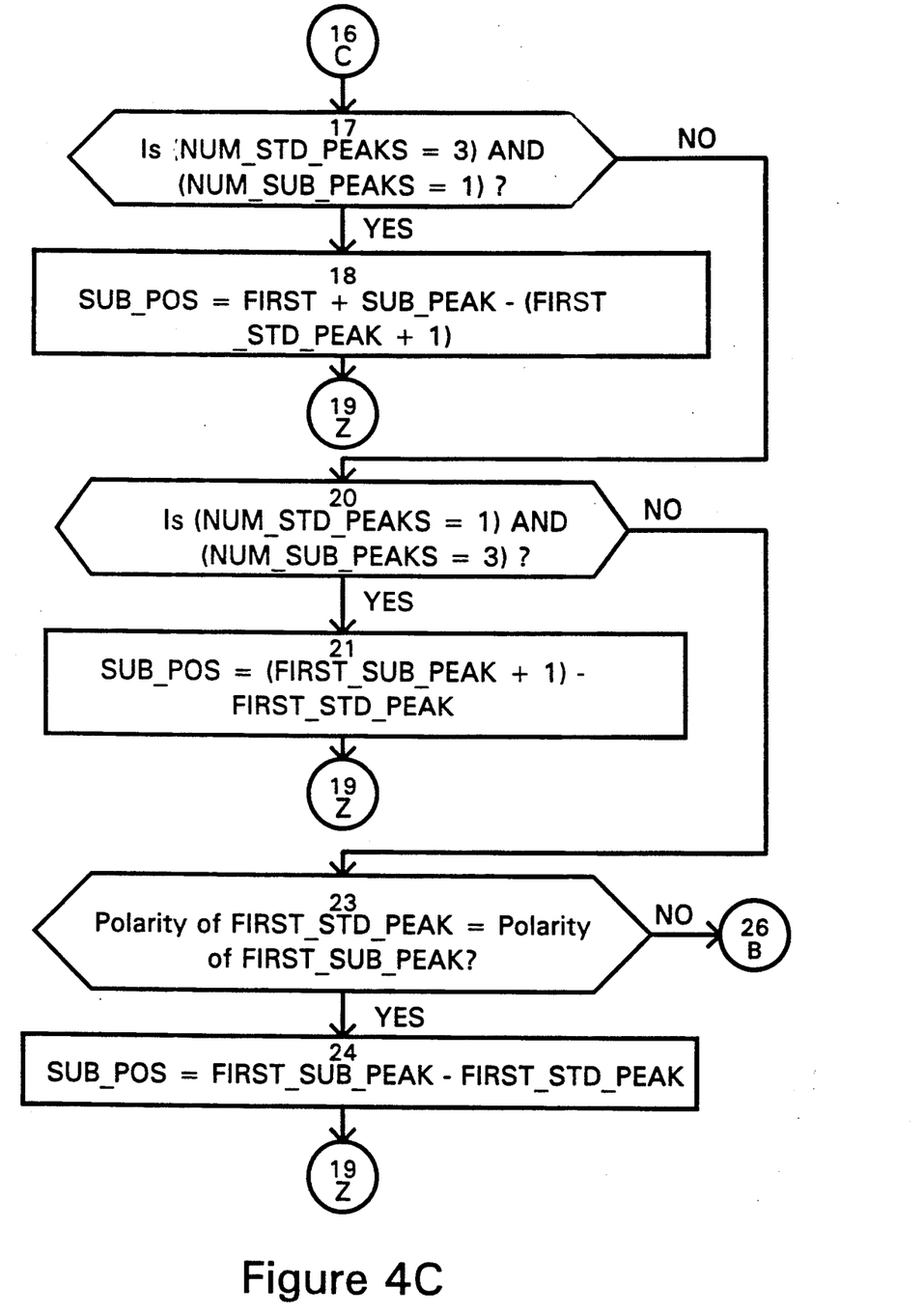
Figure 4D:
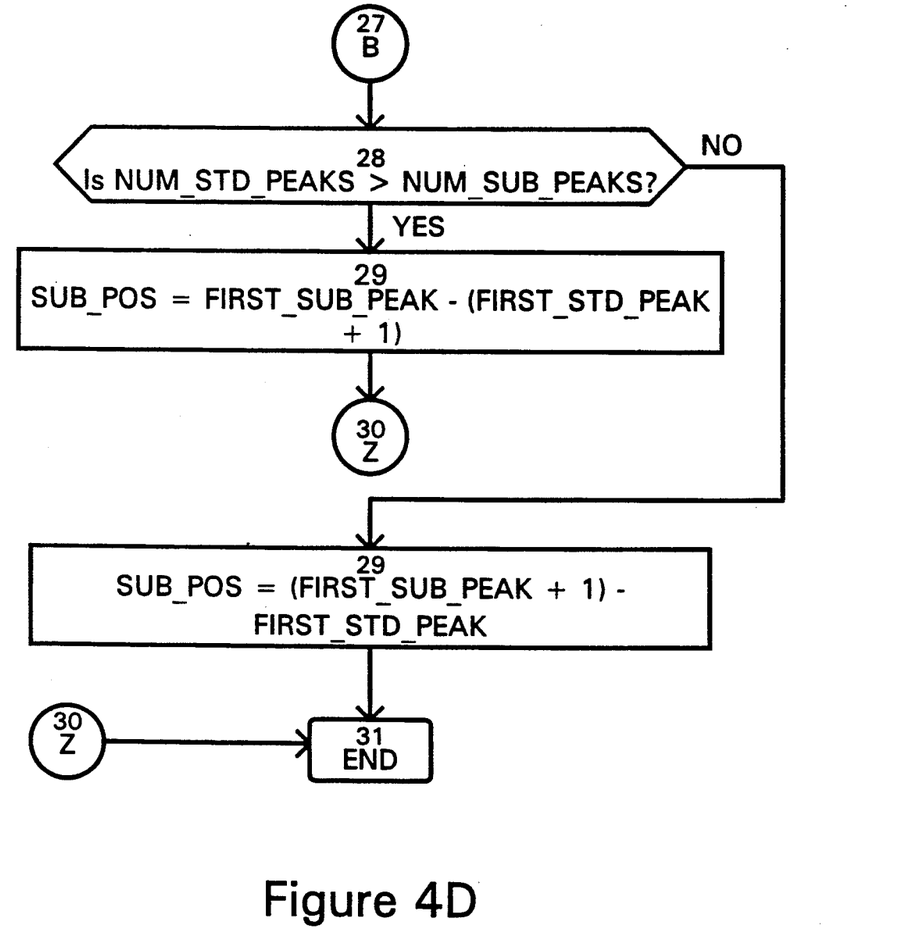

After all peaks of a complex have been captured, it is either used for maintenance of the standard or it is compared against the standard and scored. A flow chart describing the identification and capture of a complex is shown in FIGS. 3A-3B.

While the microprocessor determines that the heart is in a normal rhythm, it generates and maintains a standard of an intracardiac complex. This standard changes over time to adapt to natural physiological changes that occur in the heart. This standard is an averaged characterization of a number of normal intracardiac complexes.

A heart is defined to be in normal rhythm when a running average of the intervals between each complex is above a threshold value. This insures that the heart has been beating slowly for the last few beats and is not in a tachycardia or exercise situation.

A number of complexes are averaged together to produce the standard. There must be high confidence that each complex averaged into the standard is a normal intracardiac complex. The interval preceding that complex must not be a short interval and the current diagnosis must be normal. A new standard is produced every few intervals (e.g. 10-50). When the device is operating with variable gain (controlled by the waveform analyzer's amplifier), all complexes incorporated into the standard complex must have been acquired at the same gain setting.

Figure 6:
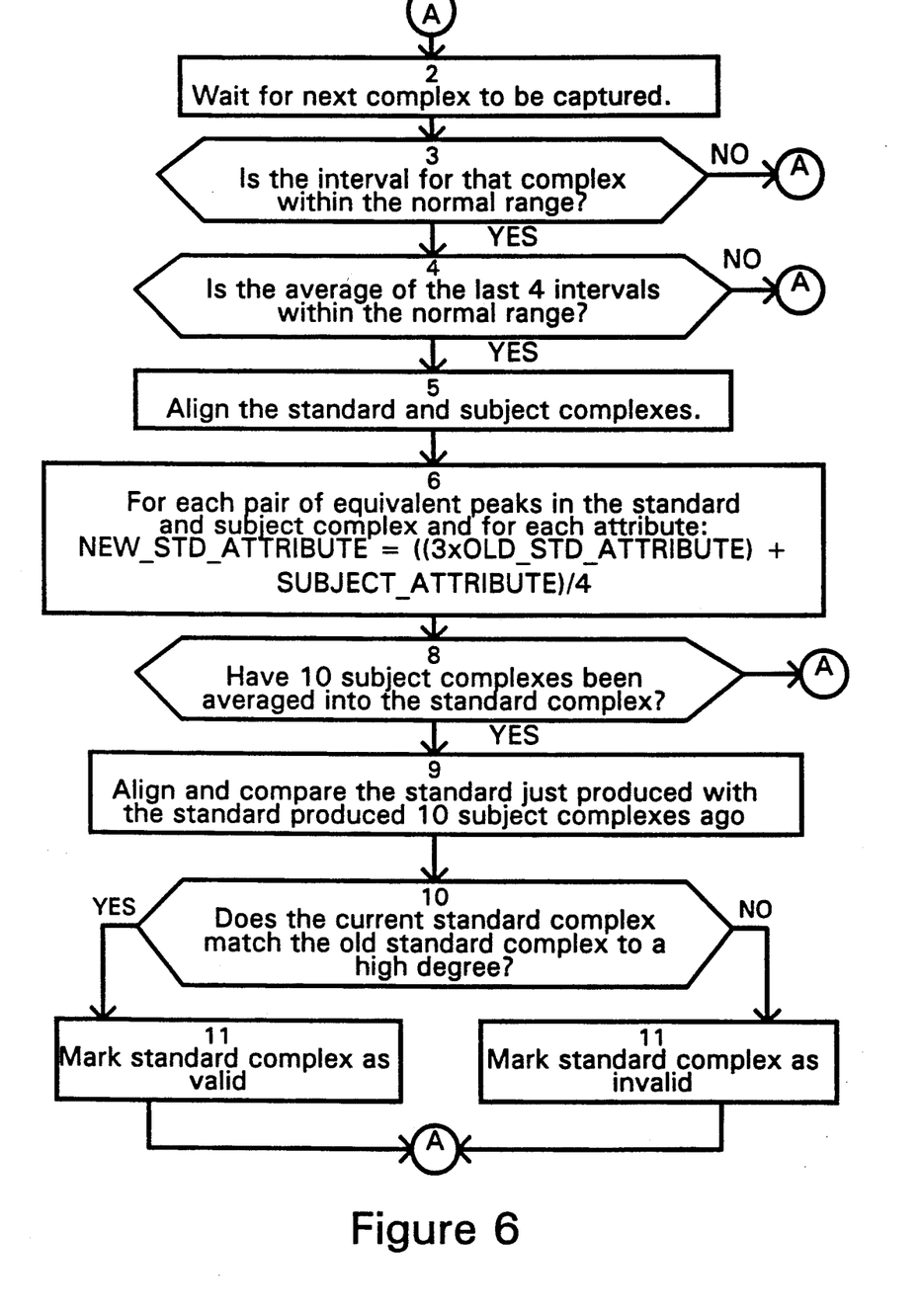
FIG. 6 is a flow chart describing the generation and maintenance of the standard complex.

The microprocessor recognizes when there has been an abrupt change in the normal rhythm and declares the standard to be invalid for the time it takes to generate a new standard. FIG. 6 provides a more detailed description of the standard complex maintenance program.

When rhythm classification is needed for a series of complexes, updating of the standard is terminated and comparison of the subject complexes to the standard complex is begun.

If the standard complex declares itself to be invalid, then no comparisons are performed, no scores are produced, and the program desiring the result of these comparisons is notified. If the standard complex is good, comparison is begun.

Comparison of two complexes is accomplished in three stages. In the first stage the gain setting of the subject complex is checked against the gain setting of the standard complex. If they differ, the comparison process is terminated and the subject complex is assigned a score of zero. The second step adjusts the complexes so their major peaks are aligned. A peak-by-peak comparison is then done to produce a score which reflects the similarity of the subject complex to the standard complex.

Alignment of complexes is based upon the number and polarity of peaks above the upper threshold (called Upeaks-below) for each complex. The program used for alignment assumes that: (1) Peaks within a complex grow in size until a dominant peak (or 2 peaks) is reached and then decrease in size; (2) subsequent peaks have opposing polarities; and (3) no non-Upeak exists between 2 Upeaks (big-small-big is not allowed). The program to align the complexes is shown in FIGS. 4A-4D. The program attempts to match the polarities of the Upeaks in each complex and, if the number of Upeaks differ, to place the dominant peak of the complex with fewer peaks in the center of the Upeaks of the complex with more peaks.

The result of the alignment process is a pointer to the peak of the subject complex where comparison is to begin. Comparison is always started at the first peak of the standard complex. The score for the subject complex is set to zero, initially. Each peak in the standard complex is compared to its equivalent peak in the subject complex. Points are subtracted or added to the score depending on the significance of the peaks compared and how well they match. Care is taken to handle peaks of either complex which have no equivalents.

Figure 5A:
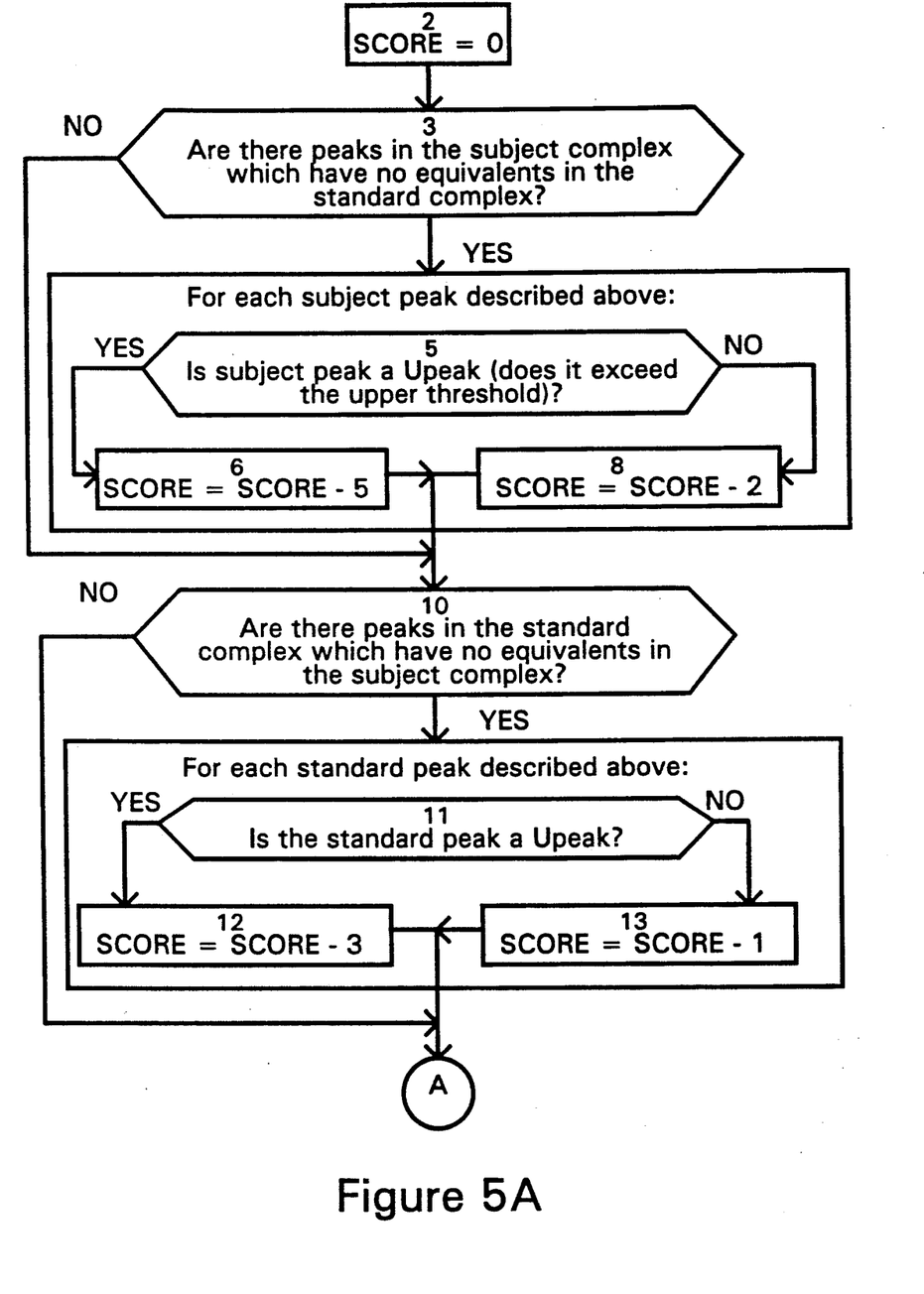
FIGS. 5A and 5B, when connected together, are a flow chart describing the comparison of waveform complexes.
Figure 5B:
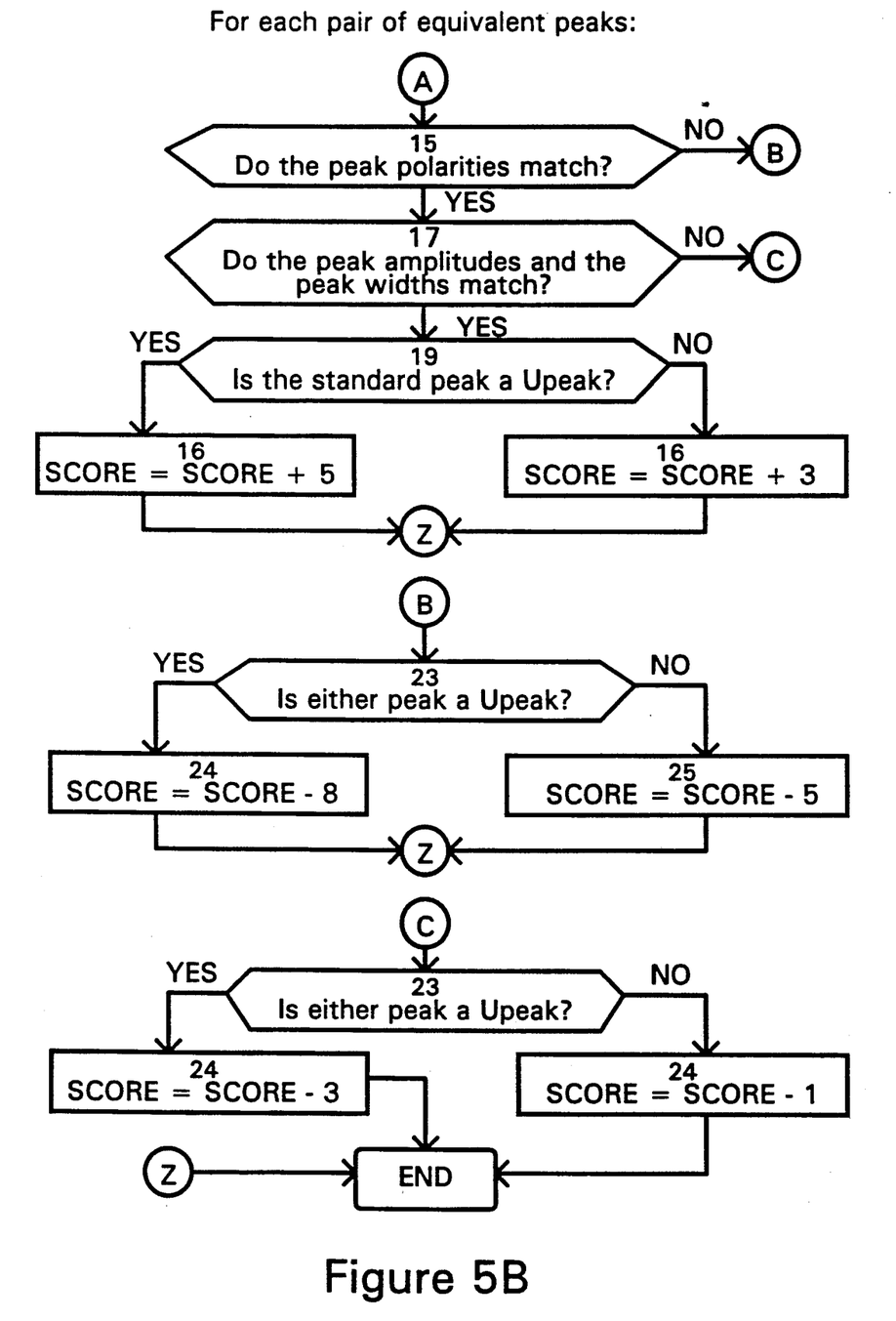

For example, peaks of opposing polarities draw a 5 point penalty minimum. If either of these two peaks are Upeaks, 3 more points are subtracted. Peaks whose polarities and amplitudes match yet have different widths are treated less harshly. These peaks draw a 1 point penalty minimum, 2 more points are subtracted if either peak is a Upeak. If two peaks match in all three categories a minimum of 2 points is awarded, 3 more points are added if the standard peak is a Upeak. A detailed description of the program is shown in FIGS. 5A-5B.

The result of the comparison process is a numeric score which can range from the negative integers into the positive integers up to the maximum score possible. The maximum score possible is the one itself. A negative or low score indicates a poor similarity between the standard and subject complex. The closer a score is to the maximum possible score, the closer the subject complex resembles the standard complex. These individual complex scores can be accumulated to produce an aggregate score for a series of complexes.

It can be seen that a novel medical device has been provided for the maintenance of a standard complex, the capture of subject complexes, comparison of subject complexes to standard complexes, and the generation of a measure of their similarity.

Although an illustrative embodiment of the invention has been shown and described, it is to be understood that various modifications and substitutions may be made by those skilled in the art without departing from the novel spirit and scope of the present invention.

What is claimed is:

1. A medical device for monitoring waveform complexes of intracardiac electrograms, which comprises:
   electrode means adapted to be coupled to a patient's heart;
   sensing means having an input coupled to said electrode means for sensing analog intracardiac electrograms;
   analog to digital converter means for converting the analog intracardiac electrogram to digital form;
   means for examining the intracardiac electrogram, said examining means comprising means for determining, with respect to a waveform peak of said digitized intracardiac electrogram, its amplitude, width and polarity, to provide identification criteria;
   means for storing said identification criteria;

means for averaging a plurality of waveform complexes to provide a standard complex and means for periodically operating said averaging means when a predetermined number of waveform complexes have occurred.

2. A medical device for monitoring waveform complexes of intracardiac electrograms, which comprises:
   electrode means adapted to be coupled to a patient's heart;
   sensing means having an input coupled to said electrode means for sensing analog intracardiac electrograms;
   analog to digital converter means for converting the analog intracardiac electrogram to digital form;
   means for examining the intracardiac electrogram, said examining means comprising means for determining, with respect to a wave from peak of said digitized intracardiac electrogram, its amplitude, width and polarity, to provide identification criteria;
   means for storing said identification criteria; and
   means for concluding if the examined peak is within the same waveform complex as the previous peak.

3. A device as defined by claim 2, said concluding means comprising means for determining whether the examined peak occurred within a predetermined time after the occurrence of a previously identified peak.

4. A device as defined by claim 2, said concluding means comprising means for determining whether the examined peak occurred within a predetermined time after occurrence of a first examined peak of a new waveform complex.

5. A device as defined by claim 2, said concluding means comprising means for determining whether a predetermined maximum number of peaks have occurred.

6. A device as defined by claim 2, said concluding means comprising means for determining (a) whether the examined peak occurred within a predetermined time after the occurrence of a previously examined peak, (b) whether the examined peak occurred within a predetermined time after occurrence of a first examined peak of a new waveform complex, and (c) whether a predetermined maximum number of peaks have occurred.

7. A device as defined by claim 1, said storing means comprising means for storing a standard waveform complex; and further including means for comparing peaks of subsequent complexes with the peaks of a stored standard complex, means for aligning subsequent complexes with a standard complex, and means for providing a score associated with the comparisons and alignment.

8. A device as defined by claim 7, said aligning means comprising means for determining the number of peaks in each complex which exceed a predetermined upper threshold, means for determining the first peak for each complex which exceeds said predetermined upper threshold, means for matching the polarities of said first peaks, and means for aligning the complex having fewer peaks exceeding said upper threshold with the complex having more peaks exceeding said upper threshold.

9. A self-contained implantable medical device for monitoring waveform complexes of intracardiac electrograms, which comprises:
   electrode means adapted to be coupled to a patient's heart;
   sensing means having an input coupled to said electrode means for sensing analog intracardiac electrograms;
   analog to digital converter means for converting the analog intracardiac electrogram to digital form;
   means for examining the intracardiac electrogram, said examining means comprising means for determining, with respect to a waveform peak of said digitized intracardiac electrogram, its amplitude, width, and polarity, to provide identification criteria;
   means for storing said identification criteria to provide a standard waveform complex; and
   means for comparing subsequent complexes with said stored standard complex, said comparison means including means for providing a score associated with the comparison as a weighted function of whether the compared peaks exceed a predetermined upper threshold.

10. A method for monitoring waveform complexes of intracardiac electrograms, which comprises the steps of:
    providing electrode means adapted for coupling to a patient's heart;
    sensing analog intracardiac electrograms from said electrode means;
    converting the analog intracardiac electrograms to a digital format;
    examining the intracardiac electrogram, said examining step comprising the step of determining, with respect to a waveform peak of said digitized intracardiac electrogram, its amplitude, width and polarity, to provide identification criteria;
    storing said identification criteria; and
    periodically averaging a plurality of waveform complexes to provide a standard complex when a predetermined number of waveform complexes have occurred.

11. A method of monitoring waveform complexes of intracardiac electrograms, which comprises the steps of:
    providing electrode means adapted for coupling to a patient's heart;
    sensing analog intracardiac electrograms from said electrode means;
    converting the analog intracardiac electrograms to a digital format;
    examining the intracardiac electrogram, said examining step comprising the step of determining, with respect to a waveform peak of said digitized intracardiac electrogram, its amplitude, width and polarity, to provide identification criteria;
    storing said identification criteria; and
    concluding if the examined peak is within the same waveform complex as the previous peak.

12. A method as defined by claim 11, said concluding step including the step of determining whether the examined peak occurred within a predetermined time after the occurrence of a previously-examined peak.

13. A method as defined by claim 11, said concluding step including the step of determining whether the examined peak occurred within a predetermined time after occurrence of a first examined peak of a new waveform complex.

14. A method as defined by claim 11, said concluding step including the step of determining whether a predetermined maximum number of peaks have occurred.

15. A method as defined by claim 11, said concluding step including the steps of determining whether the examined peak occurred within a predetermined time after the occurrence of a previously-examined peak, determining whether the examined peak occurred within a predetermined time after occurrence of a first examined peak of a new waveform complex, and determining whether a predetermined maximum number of peaks have occurred.

16. A method as defined by claim 10, in which the storing step comprises the step of storing a standard waveform complex.

17. A method as defined by claim 16, including the step of recognizing a significant change in the stored standard complex and generating a new standard complex if a significant change has occurred.

18. A method as defined by claim 16, including the steps of comparing peaks of subsequent complexes with peaks of a stored standard complex, aligning subsequent complexes with a stored standard complex, and providing a score associated with the comparisons and alignment.

19. A method as defined by claim 16, including the steps of comparing subsequent complexes with a stored standard complex, said comparison step including the step of aligning major peaks of said complexes and providing a score associated with the comparison.

20. A method as defined by claim 19, in which said score has values that are indicative of the similarity or dissimilarity of the compared peaks.

21. A method as defined by claim 19, in which said score has values that are indicative of the nature of the compared peaks.

22. A method of comparing a digitized subject electrogram complex with a digitized standard electrogram complex to generate a score which is a measure of their similarity or dissimilarity, each complex having a plurality of peaks with each peak being characterized by an amplitude, width and polarity, said method comprising the steps of:
   (a) determining, for each complex, the amplitude, width and polarity of each peak;
   (b) aligning said subject complex with said standard complex;
   (c) initializing said score;
   (d) comparing the amplitude, width and polarity of peaks within said subject complex with corresponding peaks within said standard complex; and
   (e) increasing or decreasing said score in a manner weighted as a function of whether the amplitude of either of the compared peaks exceeds a predetermined threshold.

23. A method of comparing a digitized subject electrogram complex with a digitized standard electrogram complex to generate a score which is a measure of their similarity or dissimilarity, each complex having a plurality of peaks with each peak being characterized by an amplitude, width and polarity, said method comprising the steps of:
   (a) determining, for each complex, the amplitude, width and polarity of each peak having an amplitude greater than a predetermined lower threshold;
   (b) aligning said subject complex with said standard complex;
   (c) defining those peaks having an amplitude above a predetermined upper threshold as Upeaks;
   (d) determining for each peak in said subject complex if there is a corresponding peak in said standard complex and subtracting from said score a relatively greater amount if there is no corresponding peak and said subject peak is an Upeak and a relatively lesser amount if there is no corresponding peak and said subject peak is not an Upeak;
   (e) determining for each peak in said standard complex if there is a corresponding peak in said subject complex and subtracting from said score a relatively greater amount if there is no corresponding peak and said standard peak is an Upeak and a relatively lesser amount if there is no corresponding peak and said standard peak is not an Upeak;
   (f) for each remaining pair of corresponding peaks, determining if said subject complex peak has the same polarity as said standard complex peak and if said peaks have a different polarity subtracting a relatively greater amount from said score if either peak is an Upeak and a relatively lesser amount if neither peak is an Upeak; and
   (g) for each remaining pair of corresponding peaks having the same polarity, determining if both the amplitude and width of each subject complex peak is within a predetermined error of the amplitude and width of said corresponding standard complex peak and if the amplitude and width are within said predetermined error, adding a relatively greater amount to said score if said standard complex peak is an Upeak and if not, adding a relatively lesser amount to said score; and if either of the amplitude or width is not within said predetermined error, subtracting a relatively greater amount if either of said peaks is an Upeak and a relatively lesser amount if neither of said peaks is an Upeak.

* * * * *